US005603695A

United States Patent [19]

Erickson

[11] Patent Number: 5,603,695

[45] Date of Patent: Feb. 18, 1997

[54] DEVICE FOR ALKALIZING LOCAL ANESTHETIC INJECTION MEDICATION

[76] Inventor: Kim Erickson, 7310 Oliver Woods, Grand Rapids, Mich. 49546

[21] Appl. No.: 475,641

[22] Filed: Jun. 7, 1995

[51] Int. Cl.[6] .......... A61M 37/00

[52] U.S. Cl. .......... 604/89; 604/82; 604/87; 604/232

[58] Field of Search .......... 604/82, 86, 87, 604/88, 89, 91, 200, 201, 232, 310, 311, 187, 195, 413, 412, 414

[56] References Cited

U.S. PATENT DOCUMENTS

| | | | |
|---|---|---|---|
| 4,607,671 | 8/1986 | Aalto et al. | 604/412 X |
| 5,247,972 | 9/1993 | Tetreault | 604/187 X |
| 5,330,426 | 7/1994 | Kriesel et al. | 604/89 |
| 5,445,631 | 8/1995 | Uchida | 604/413 X |

OTHER PUBLICATIONS

Steinbrook R A. Hughes N. et al.: Effects of Alkalinization of Lidocaine on the Pain of Skin Infiltration and Intravenous Catheterization J. Clin Anesth, 5 Nov./Dec. 1993, 456–456.

Armel H E and Horowitz M., Alkalinization of Local Anesthesia.

Metzinger, Stephen E, et al., Local Anesthesia in Blepharoplasty: A New Look.

McKay, Warren M D, Sodium Bicarbonate Attenuates Pain on Skin Infiltration with Lidocaine with or without Epinephrine. Anesth Analg. 1987. 66, 572–574.

Morris, Richard, MBBS, FFARCS et al. Comparison of Pain Associated with Intradermal and Subcultaneous Infiltration with Various Local Anesthetic Solutions, Anesth Analg. 1987. 66, 1180–1182.

Christoph R A Buchanan L., et al.: Pain Reduction in Local Anesthetic Administration Through pH Buffering. Annal of Emerg Med, 1988. 17, 117–120.

Stewart J H Chinn S E et at: Neutralized lidocaine with Epinephrine for Local Anesthesia. J. Dermatol Surg Oncol 1990. 16, 842–845.

*Primary Examiner*—Corrine M. McDermott
*Assistant Examiner*—N. Kent Gring
*Attorney, Agent, or Firm*—Alfred E. Miller

[57] ABSTRACT

A disposable cartridge containing a buffering solution for attachment to a local anesthetic carrier in order to alkalize the anesthetic. The cartridge is provided with a needle which permits the buffering solution to enter the carrier and mix with the anesthetic solution.

14 Claims, 3 Drawing Sheets

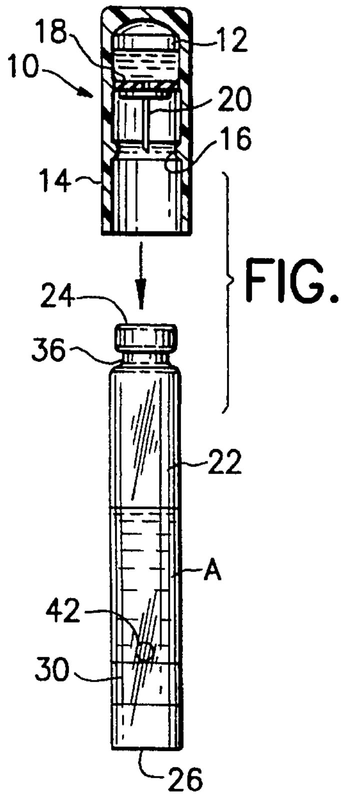
FIG. 1
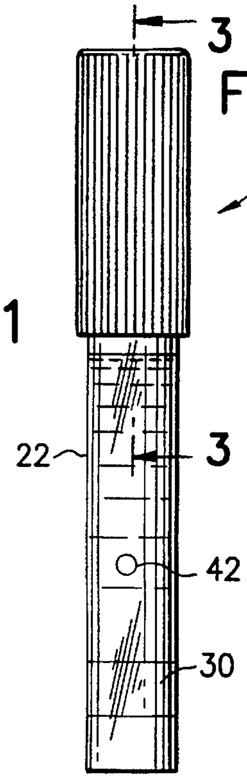
FIG. 2
FIG. 3
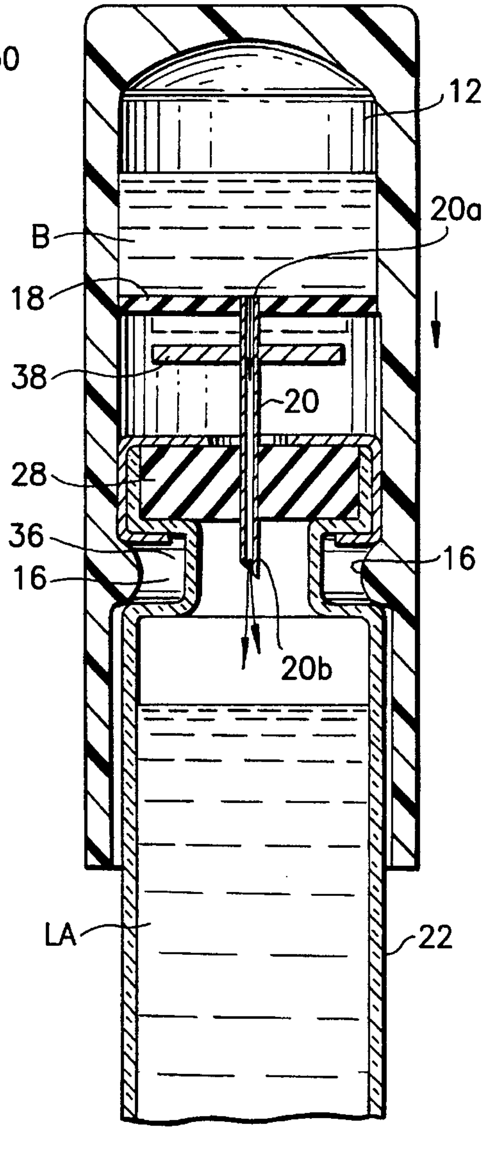
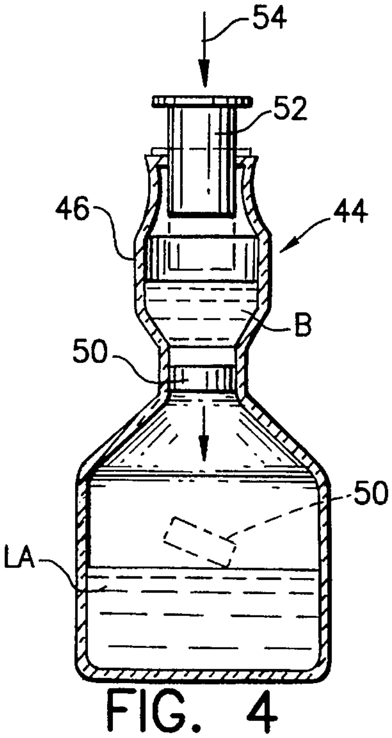
FIG. 4

DEVICE FOR ALKALIZING LOCAL ANESTHETIC INJECTION MEDICATION

The present invention relates to a device for reducing the pain and discomfort commonly associated with the administration of a local anesthetic injection.

It is well know that local anesthetics have been used to locally numb areas or regions of the body so that surgical treatments can be performed without resorting to a general anesthesia. A common example is the local anesthesia injection by a dentist when working in the mouth area.

Common local anesthetics currently employed may be lidocaine or the like. Most, if not all, local anesthetic formulations are acidic, with a pH below 7.0. It has been determined by scientific investigations that the acidic nature of a local anesthetic formulation principally causes the pain and discomfort associated with an interdermal injection. lidocaine, for example, is manufactured with a pH of 4.5 (range 3.5 to 5.5), which makes it more soluble and stable and has the desirable result of an extended shelf life.

In order to alleviate the pain experienced by local anesthetic injections doctors often add sodium bicarbonate ($NaHCO_3$) to the selected anesthetic in order to alkalize the medication. Several articles have been written on the subject matter such as follows:

Christoph R. A. Buchanan L., et al.: Pain Reduction in Local Anesthetic Administration Through pH Buffering. Annal of Emerg Med 1988. 17, 117–120.

Stewart J. H. Chinn S. E. et al.: Neutralized Lidocaine with Epinephrine for Local Anesthesia. J. Dermatol Surg Oncol 1990. 16, 842–845.

Steinbrook R. A. Hughes N. et al.: Effects of Alkalinization of Lidocaine on the Pain of Skin Infiltration and Intravenous Catheterization. J. Clin Anesth, 5 Nov./Dec. 1993, 456–456.

Armel H. E. and Horowitz M., Alkalinization of Local Anesthesia with Sodium Bicarbonate-Preferred Method of Local Anesthesia. Urology. 1994. 43, 101.

It is known that when a medical buffering solution, such as sodium bicarbonate, is added just prior to injection, the result is a decrease in pain experienced by the patient. On the other hand, if the buffering solution is added to the anesthetic well prior to the injection, such as at the factory site, the efficacy of the medication is significantly reduced, and the end result is unsatisfactory. Consequently, it is extremely important that a device be developed which can mix a buffering solution with a local anesthetic prior to use, and which is disposable.

Presently, sodium bicarbonate is added to a local anesthetic by a doctor, it is done by using a syringe to draw in a certain amount of sodium bicarbonate solution from a bottle, or vial and then added to an anesthetic bottle or vial. The two agents are thereafter physically mixed by tipping or turning the bottle up and down. This method is clearly inconvenient, whereas my present device permits the above procedure to be performed in a quick and easy manner.

It is an object of the present invention to provide a disposable device or cartridge having a buffering solution, such as sodium bicarbonate, but not limited thereto, which can be removably attached to a local anesthetic carpule®, which is capable of easily and rapidly transferring the buffering solution to the anesthetic.

Another object of the present invention is to provide a dual compartment vial system for adding a buffering solution in an upper compartment to a local anesthetic in a lower compartment whereby the solutions are mixed and the resultant solution can be withdrawn by a syringe, such as a standard medical syringe.

A further feature of the present invention is to provide a cartridge for containing the buffering solution having an internal means for transferring the buffering solution to a standard dental carpule. However, different size carpules, or similar vehicles, can be used to handle the medication mixture.

It is another object of the present invention to provide a sealed carrier for a buffering solution that can be easily and rapidly attached to a standard dental carpule, and is designed for a single usage and then discarded.

The above and other objects and features of the invention will become apparent by reference to the following description of my invention and the drawings.

BRIEF DESCRIPTION OF THE DRAWINGS

FIG. 1 is a sectional view of the device for alkalizing local injection medication prior to attachment to the anesthetic carrier in accordance with the teachings of the present invention.

FIG. 2 is a front elevation of the cartridge assembled with the anesthetic carrier.

FIG. 3 is an enlarged view taken along the lines 3—3 of FIG. 2.

FIG. 4 is a sectional view of alternate embodiment of the present invention.

DESCRIPTION OF THE PREFERRED EMBODIMENTS

Figure 5:
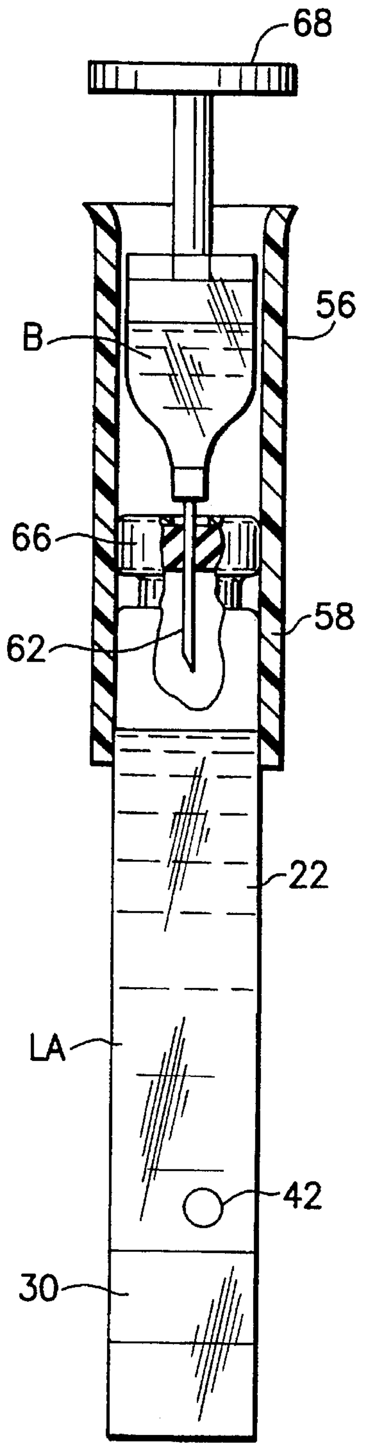
FIG. 5 is a sectional view of another embodiment of the device for alkalizing local injection medication.

Referring to FIGS. 1–3 the device for alkalizing local injection medication in the dental and medical field is shown as a cartridge referred to generally by the reference numeral 10. The cartridge 10, which is preferably manufactured of plastic, is generally cylindrical and has an enclosed chamber 12 provided with a buffering solution B, such as sodium bicarbonate. Depending from the bottom of the chamber 12 is a cylindrical protective skirt 14 provided with interior, spaced bumps 16. It should be apparent that the skirt 14 which surrounds the needle 20 functions as a safety feature protecting the user from accidental injury by the needle. The cartridge is intended for a single use. The seal 18 for chamber 12 is constituted of rubber, or some other material that can be penetrated or punctured. Substantially centrally located in the seal 18 is a needle 20. The needle, although inserted within the seal 18, does not penetrate initially into the chamber 12.

The above-described cartridge 10 functions in conjunction with a local anesthetic carrier such as a dental carpule 22. The carpule is initially open ended at opposite ends 24 and 26 respectively. One end 24, which is the needle end, is closed by a rubber membrane 28 while the opposite end 26 is closed by a rubber plunger 30 after the anesthetic liquid placed therein. However, the plunger 30 is spaced interiorly from the adjacent end of the carpule. The carpule 22 is of the type currently used by health professionals and is a glass tube having a premeasured amount of local anesthetic LA in it.

The procedure in connection with the actuation of the device is as follows: The dentist, or any health professional, pushes the cartridge 10 on the carpule 22 from the position shown in FIG. 1 to the position shown in FIG. 2. In this connection, the bumps 16 on the inner surfaces of the skirt 14 are utilized to pass over the end 24 of the carpule 22 to position the carpule within the cartridge, and to ride into the groove 36 forming the neck of the carpule. A stop member 38 affixed to the needle 20 is located within the skirt 14. When the cartridge is pushed in the direction of the arrow 40 the stop mechanism 38 moves to the position shown in the dotted lines in FIG. 3 abutting the seal 18, and the needle end 20*a* is forced through seal 18 into chamber 12. At the same time the other end 20*b* of the needle is forced through the rubber membrane 28 and enters the carpule 22 so that the buffering solution B enters the carpule 22 having the local anesthetic therein, the rubber stopper 30 in the opposite end of the carpule moves toward the adjacent end so that added volume of buffering solution can be accommodated in the carpule. When this occurs the buffering solution, such as sodium bicarbonate, or sodium hydroxide, flows from the chamber 12 in the cartridge 10 into the carpule 22. Thereafter, the two solutions are mixed with or without the employment of a mixing ball 42. The cartridge 10 can then be discarded.

When it is desired to use the carpule in connection with injecting a local anesthetic into a patient the carpule having the buffering solution combined with the anesthetic is placed into a syringe (not shown), and the plunger 30 of the carpule is engaged by an element of the syringe to force the local anesthetic into the area of the body that is to be treated. Since the local anesthetic has been alkalized a considerable amount of the pain associated with local anesthetic injections has been eliminated.

FIG. 4 shows another embodiment of the present invention which is a dual compartment vial referred to generally by the reference numeral 44 having an upper compartment 46 and a lower compartment 48. The upper compartment 46 is provided with a buffering solution B such as sodium bicarbonate, while the lower compartment 48 has a local anesthetic solution LA. The upper and lower compartments are kept separate initially by means of an internal plunger 50. Closing the open top of compartment 46 is a second stopper-plunger 52.

In order to mix the buffering solution B with the local anesthetic LA downward pressure is applied on the plunger 52 as indicted by arrow 54. This pressure increases the hydrostatic pressure in compartment 46 which forces the internal plunger 50 in to the lower compartment 48. The two component solutions B and LA are then mixed and the mixture can be withdrawn through the stopper-plunger 52 by means of a standard medical syringe.

An alternate embodiment of the present invention is shown in FIG. 5 in which a syringe 56 having a buffering solution therein is provided with a cylindrical protective skirt 58. The needle 62 of the syringe is positioned within the skirt 58.

In order to connect or apply the syringe 56 to the carpule 22 the skirt of the syringe is force fitted over the needle end of the carpule 22, and is pushed onto the carpule to form a friction fit over the outer surface of the carpule. When that happens the needle punctures the membrane 66 of the carpule and the buffering solution in the syringe can be transferred to the carpule by pressing the plunger 68 downwardly so that the solution therein is completely expelled or transferred to the carpule 22.

It should be noted that the present devices for alkalizing local anesthetic medication can be utilized in general medical, dental and veterinary applications, and complies strictly with sanitary requirements by being packaged in a sterile manner.

Figure 6:
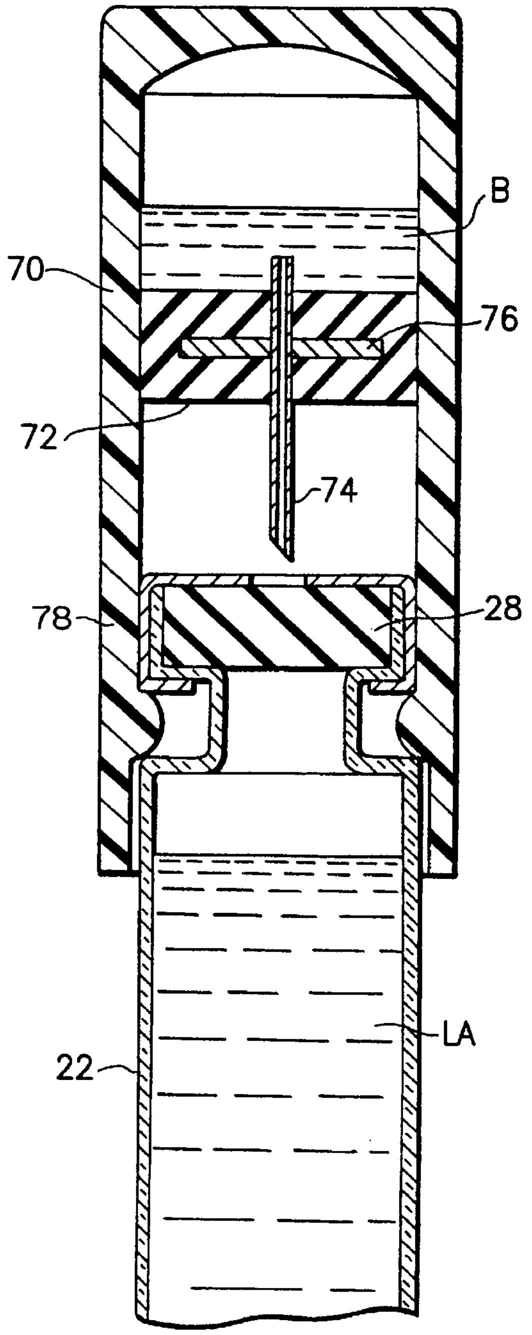
FIG. 6 is a sectional exploded view of an alternate embodiment for a device for alkalizing local injection medication.
Figure 7:
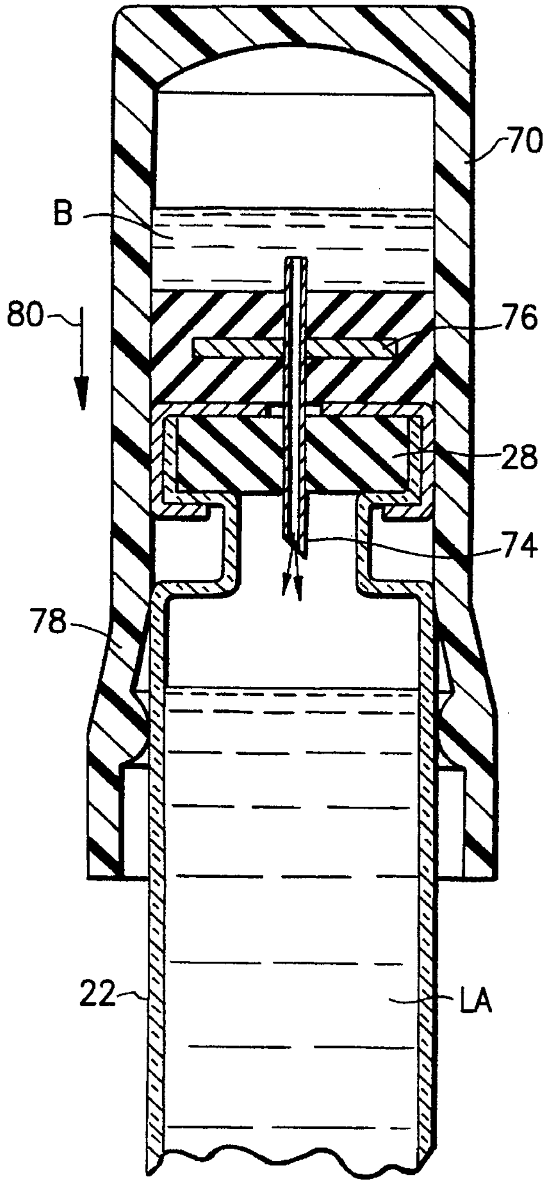
FIG. 7 is a sectional view of the device shown in FIG. 6 with the device being applied to a carpule for transfer of the buffering solution to the carpule containing the local injection medication.

Referring now to FIGS. 6 and 7, an alternate embodiment of the present invention is shown in which a carpule 22, such as a standard dental carpule, although not restricted thereto, is provided with a buffering device 70 holding a buffering solution. The device has an internal stopper 72 having a needle 74. The needle is firmly held in the stopper 72 by means of a rigid plate 76 of metal, plastic or any other suitable material. The device 70 is provided with a depending protective skirt 78. FIG. 7 shows the buffering device being pushed in the direction of arrow 80 so that the skirt 78 fits frictionally over one end of the carpule 22 while needle 74 punctures the diaphragm 28 of the carpule 22. When the device and the carpule are squeezed together the buffering solution is injected in the local anesthetic carpule through the needle 74.

Figure 8:
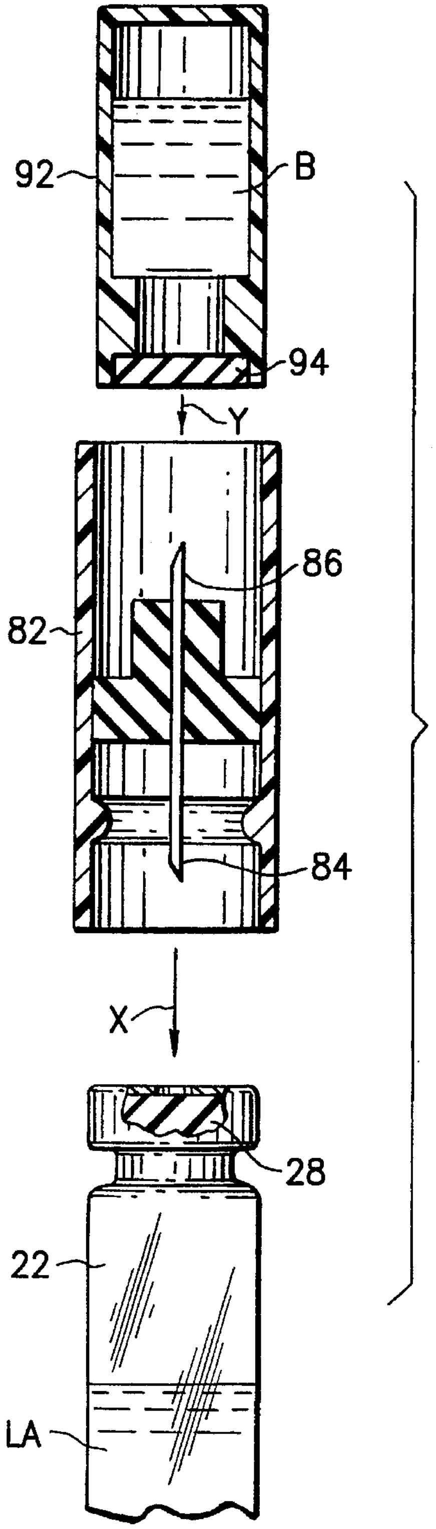
FIG. 8 is an exploded view of an embodiment of the present invention having an intermediate cylinder with a double-edged needle.

FIG. 8 is another alternate embodiment of the present invention and as illustrated in FIGS. 1–3*a* standard dental carpule 22 is provided with a local anesthetic, said carpule 22 having a rubber diaphragm 28 at one end and a rubber plunger or stopper (not shown) at the opposite end of the type shown in FIG. 1.

The present device includes an intermediate cylinder 82 which is open on both ends and is provided with a double-ended needle 84–86 which projects in opposite directions in the cylinder, and both the needles are protected by depending skirts 88 and 90, respectively. The cylinder 82 is located between the carpule 22 and a buffer cartridge 92 which contains a predetermined amount of buffering solution.

In order to activate and alkalize the local anesthetic in the dental carpule 22 the carpule in the cylinder 82 is pushed on the carpule in the direction shown by the arrow X, with the needle 86 puncturing the diaphragm 28 of the carpule while the cartridge 92, with the buffering solution is slid on the back end of the cylinder 82, as shown by the arrow Y.

When the carpule 22, cylinder 82 and cartridge 92 are squeezed together the needle 84 penetrates through diaphragm 28 of the cartridge 92 while the needle 86 penetrates through rubber stopper 94 of the carpule thus permitting the transfer of the buffering solution in the cartridge 92 to the carpule by means of said double ended needle 84–86 in the cylinder 82.

Although the present invention has been disclosed and described with reference to the two embodiments thereof, it should be apparent that other variations and modifications may be made, and it is intended that the following claims cover said variations within the true spirit and scope of the invention.

What I claim is:

1. A device for alkalizing a local anesthetic injection comprising in combination a local anesthetic carrier being substantially cylindrical and having opposite ends and a bottom, a disposable cartridge having opposite ends and containing a buffering solution having means at one end of the cartridge for removably securing said cartridge to said anesthetic carrier, hollow needle means on said end of the cartridge communicating with said buffering solution for transferring said buffering solution from said cartridge through one end of said carrier, a movable stopper in the bottom of said carrier spaced adjacent to the opposite end of said carrier whereby when said buffering solution enters said carrier said stopper moves toward said opposite end in order to enlarge the interior space of said carrier to accommodate the buffering solution that is transferred therein from said cartridge.

2. The device as claimed in claim 1 wherein said buffering solution is sodium bicarbonate.

3. The device as claimed in claim 1 wherein said buffering solution is sodium hydroxide.

4. The device for alkalizing local injection medication in combination with a local anesthetic carrier as claimed in claim 1 wherein said local injection medication is lidocaine and said buffering solution is sodium bicarbonate.

5. The device as claimed in claim 1 wherein said carrier is provided with a mixing member for mixing the two components of the medication.

6. A device for raising the pH level of a local anesthetic medication from acidic to less acidic and having a local anesthetic carrier and a cartridge, said cartridge having two ends and a buffering solution and being capable of being removably attached to said carrier comprising: a hollow needle projecting from one end of the cartridge and in communication with said buffering solution, a skirt on one end of said cartridge surrounding said needle, a frictional surface on an inside surface of said skirt whereby the skirt of the carrier is frictionally attached to one end of said carrier, said one end of said carrier having an puncturable seal, and said needle puncturing said seal when said when said cartridge is forced against aid one end of the carrier to permit the transferring of said buffering solution from said cartridge to said carrier.

7. The device as claimed in claim 6 wherein said carrier is a dental carpule.

8. The device as claimed in claim 6 wherein said carrier is cylindrical and said puncturable seal is a rubber member, said cartridge being cylindrical and provided with an open ended cylindrical skirt having a frictional internal surface at one end of said cartridge, said skirt being placed over said one end of the carrier, and needle means on said cartridge projecting into the interior of said skirt so that needle means is capable of penetrating through said rubber member in order to transfer the buffering solution in said cartridge to said carrier.

9. The device as claimed in claim 6 wherein said needle means communicated the cartridge with said carrier when said cartridge is pushed to a predetermined position over said one end of said dental carrier.

10. The device as claimed in claim 9 wherein said needle is provided with a stop member for permitting only limited movement of said needle into the interior of said cartridge.

11. A device for alkalizing a local anesthetic medication in combination with a carpule having said medication comprising a syringe having a buffering solution therein, said syringe having a needle at one end and a plunger at the opposite end and provided with a depending skirt, one said one end surrounding said syringe the needle of said syringe being located within said skirt, said carpule having one end with a membrane, said skirt being adopted to frictionally fit over said one end of the carpule whereby the needle punctures said membrane when said plunger is depressed and the buffering solution therein is transferred through said needle to mix the anesthetic solution in the carpule.

12. A system for alkalizing a local anesthetic medication in a carrier member comprising in combination a carrier member having said local anesthetic medication therein, an intermediate cylinder, a double-ended needle in said cylinder, a double-ended protective skirt projecting from opposite ends of said intermediate cylinder and a cartridge having a buffering solution therein, said carrier member being provided with a membrane on one end and a movable stopper at the other end, said cartridge having a closure member at one end, said intermediate cylinder having the skirt at one end being inserted over one end of said carrier member whereby one end of the double-ended needle punctures and passes through the membrane of said carrier member, and said cartridge with the buffering solution is inserted within the skin at the opposite end of said intermediate cylinder whereby the other end of the double-ended needle punctures and passes through the closure member of said cartridge thereby permitting the flow of said buffering solution from said cartridge through said double-ended needle and into said carrier member having the local anesthetic medication threrein.

13. A system as claimed in claim 12 wherein each end of said double-ended needle is provided with a depending skirt which surrounds and protects each end of the needle.

14. A device as claimed in claim 12 wherein said cartridge, double-ended needle and carrier member are squeezed together in order to cause the flow of the buffering solution to said carrier member.

* * * * *